Figure 1:
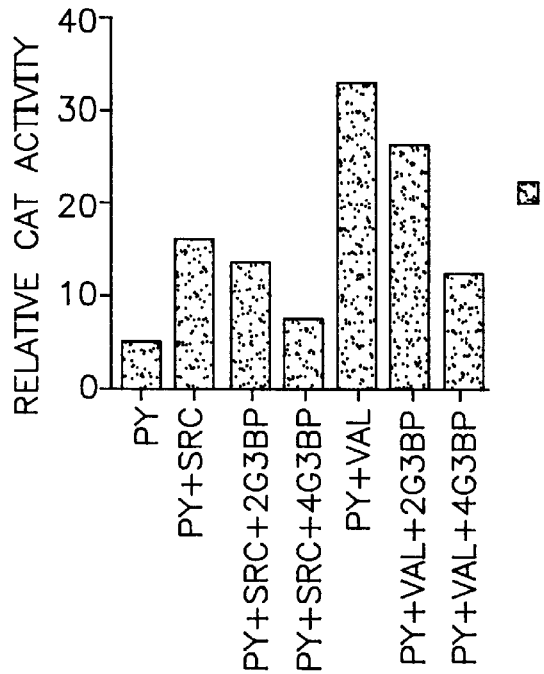

United States Patent [19]
Duchesne et al.

[11] Patent Number: 5,886,150
[45] Date of Patent: Mar. 23, 1999

[54] PEPTIDES CAPABLE OF BINDING TO THE GAP PROTEIN SH3 DOMAIN, NUCLEOTIDE SEQUENCES CODING THEREFOR, AND PREPARATION AND USE THEREOF

[75] Inventors: Marc Duchesne, Sucy En Brie; Didier Faucher, Paris; Fabienne Parker, Antony; Fabien Schweighoffer, Vincennes; Bruno Tocque, Courbevoie, all of France

[73] Assignee: Rhone-Poulenc Rorer SA, Antony Cedex, France

[21] Appl. No.: 836,791

[22] PCT Filed: Nov. 22, 1995

[86] PCT No.: PCT/FR95/01539

§ 371 Date: Jul. 11, 1997

§ 102(e) Date: Jul. 11, 1997

[87] PCT Pub. No.: WO96/16169

PCT Pub. Date: May 30, 1996

[30] Foreign Application Priority Data

Nov. 22, 1994 [FR] France ................................. 94 13955
May 16, 1995 [FR] France ................................. 95 05753

[51] Int. Cl.⁶ .............................. C07K 14/00; C07K 5/00
[52] U.S. Cl. ............................................ 530/350; 530/300
[58] Field of Search .................................... 530/300, 350, 530/358; 514/2

[56] References Cited

FOREIGN PATENT DOCUMENTS

| | | |
|---|---|---|
| 349 071 | 1/1990 | European Pat. Off. . |
| 496 162 | 7/1992 | European Pat. Off. . |
| 2 694 296 | 2/1994 | France . |
| WO 91/02749 | 3/1991 | WIPO . |
| WO 94/16069 | 7/1994 | WIPO . |

OTHER PUBLICATIONS

Ngo et al., Computational complexity, protein structure prediction, and the levinthal paradox, The Protein Folding Problem and Tertiary Structure Prediction, pp. 433–440, 1994.

Burd et al., Primary stryctures of the heterogeneous nuclear ribonucleoprotein A2, B1, and C2 proteins: A diversity of RNA binding proteins is generated by small peptide inserts, Proc. Natl. Acad. Sci., vol. 86, pp. 9788–9792, Dec. 1989.

Janssen et al., SH3 Binding of GAP–Associated p. 62: Linking Protein Tyrosine Kinases and Ras Activation in T Cells, Immunobiology, 191:2–3, 128–129 (1994).

Duchesne et al., Identification of the SH3 Domain of GAP as an Essential Sequence for Ras–GAP–Mediated Signaling, Science, 259, 525–528 (1993).

Yang et al., Solution Structure of GAP SH3 Domain by 1H NMR and Spatial Arrangement of Essential Ras Signaling–Involved Sequence, EMBO Journal, 13:6, 1270–1279 (1994).

Park et al., BUD2 Encodes a GTPase–activating Protein for Bud1/Rsr1 Necessary for Proper B ud–site Selection in Yeast, Nature, 365, 269–274 (1993).

Barfod et al., Cloning and Expression of a Human CDC42 GTPase–activating Protein Reveals a Funtional SH3–binding Domain, J. Biol. Chem., 268:35, 26059–26062, (1993).

Medema et al., GTPase–Activating Protein SH2–SH3 Domains Induce Gene Expression in a Ras–Dependent Fashion, Molecular & Cellular Biology, 12:8, 3425–3430, (1992).

Seidel–Dugan et al., Effects of SH2 and SH3 Deletions on the Functional Activities of Wild–Type and Transforming Variants of c–Src, Molecular & Cellular Biology, 12:4, 1835–1845, (1992).

Auffray et al., IMAGE: integrated molecular analysis of the human genome and its expression, C.R. Acad. Sci. III, Sci. VIE, 318, 263–272, (1995).

*Primary Examiner*—George C. Elliott
*Assistant Examiner*—Andrew Wang

[57] ABSTRACT

Peptides capable of interacting with the GAP protein SH3 domain, nucleic acid sequences coding therefor, and pharmaceutical compositions containing same, are disclosed.

7 Claims, 1 Drawing Sheet

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: protein ( v ) FRAGMENT TYPE: internal ( x i ) SEQUENCE DESCRIPTION: SEQ ID NO:1:

```
Val  Met  Glu  Lys  Pro  Ser  Pro  Leu  Leu  Val  Gly  Arg  Glu  Phe  Val  Arg
 1                  5                            10                           15
Gln  Tyr  Ile
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Xaa  Xaa  Glu  Gly  Asp  Asp  Arg  Asp  Asn  Arg  Leu  Leu  Gly  Pro
 1                  5                            10
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: protein ( v ) FRAGMENT TYPE: internal ( x i ) SEQUENCE DESCRIPTION: SEQ ID NO:3:

```
Leu  Pro  Asn  Phe  Gly  Phe  Val  Val  Phe  Asp  Asp  Ser  Glu  Pro  Val  Gln
 1                  5                            10                           15
Lys
```

( 2 ) INFORMATION FOR SEQ ID NO:4:

( i ) SEQUENCE CHARACTERISTICS:

(A) LENGTH: 19 amino acids
(B) TYPE: amino acid
(C) STRANDEDNESS:
(D) TOPOLOGY: linear (i i) MOLECULE TYPE: protein (v) FRAGMENT TYPE: internal (x i) SEQUENCE DESCRIPTION: SEQ ID NO:4:

Ser Ala Thr Pro Ala Pro Ala Asp Val Ala Pro Ala Gln Glu Asp Leu
1               5                   10                  15

Arg Xaa Phe (2) INFORMATION FOR SEQ ID NO:5:

(i) SEQUENCE CHARACTERISTICS:
(A) LENGTH: 68 amino acids
(B) TYPE: amino acid
(C) STRANDEDNESS:
(D) TOPOLOGY: linear (i i) MOLECULE TYPE: protein (v) FRAGMENT TYPE: internal (x i) SEQUENCE DESCRIPTION: SEQ ID NO:5:

Arg Glu Ala Gly Glu Gln Gly Asp Ile Glu Pro Arg Arg Met Val Arg
1               5                   10                  15

His Pro Asp Ser His Gln Leu Phe Ile Gly Asn Leu Pro His Glu Val
            20                  25                  30

Asp Lys Ser Glu Leu Lys Asp Phe Phe Gln Ser Tyr Gly Asn Val Val
            35                  40                  45

Glu Leu Arg Ile Asn Ser Gly Pro Lys Leu Pro Asn Phe Ala Phe Val
    50                  55                  60

Val Phe Asp Asp
65

(2) INFORMATION FOR SEQ ID NO:6:

(i) SEQUENCE CHARACTERISTICS:
(A) LENGTH: 204 base pairs
(B) TYPE: nucleic acid
(C) STRANDEDNESS: double
(D) TOPOLOGY: linear (i i) MOLECULE TYPE: other nucleic acid
(A) DESCRIPTION: /desc = "Oligonucleotide"

(i x) FEATURE:
(A) NAME/KEY: misc_feature
(B) LOCATION: 1..204

(x i) SEQUENCE DESCRIPTION: SEQ ID NO:6:

CGTGAGGCTG GTGAGCAAGG TGACATTGAA CCCCGAAGAA TGGTGAGACA CCCTGACAGT        60

CACCAACTCT TCATTGGCAA CCTGCCTCAT GAAGTGGACA AATCAGAGCT TAAAGATTTC       120

TTTCAAAGTT ATGGAAACGT GGTGGAGTTG CGCATTAACA GTGGTGGGAA ATTACCCAAT       180

TTCGCCTTCG TCGTCTTCGA TGAT                                              204

(2) INFORMATION FOR SEQ ID NO:7:

(i) SEQUENCE CHARACTERISTICS:
(A) LENGTH: 32 base pairs
(B) TYPE: nucleic acid
(C) STRANDEDNESS: single
(D) TOPOLOGY: linear ( i i ) MOLECULE TYPE: other nucleic acid
(A) DESCRIPTION: /desc = "Oligonucleotide"

( i x ) FEATURE:
(A) NAME/KEY: modified_base
(B) LOCATION: 1..32
(D) OTHER INFORMATION: /mod_base=i
/ note= "N=Inosine"

( x i ) SEQUENCE DESCRIPTION: SEQ ID NO:7:

GTNATGGANA ANCCNTCCCC NCTNCTNGTN GG  32

(2) INFORMATION FOR SEQ ID NO:8:

( i ) SEQUENCE CHARACTERISTICS:
(A) LENGTH: 26 base pairs
(B) TYPE: nucleic acid
(C) STRANDEDNESS: single
(D) TOPOLOGY: linear ( i i ) MOLECULE TYPE: other nucleic acid
(A) DESCRIPTION: /desc = "Oligonucleotide"

( i x ) FEATURE:
(A) NAME/KEY: misc_feature
(B) LOCATION: 1..23

( i x ) FEATURE:
(A) NAME/KEY: modified_base
(B) LOCATION: 1
(D) OTHER INFORMATION: /mod_base=i
/ note= "N=Inosine"

( x i ) SEQUENCE DESCRIPTION: SEQ ID NO:8:

GAATCATCGA ANACNACGAA NCCGAA  26

(2) INFORMATION FOR SEQ ID NO:9:

( i ) SEQUENCE CHARACTERISTICS:
(A) LENGTH: 466 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:9:

```
Met Val Met Glu Lys Pro Ser Pro Leu Leu Val Gly Arg Glu Phe Val
 1               5                  10                  15
Arg Gln Tyr Tyr Thr Leu Leu Asn Gln Ala Pro Asp Met Leu His Arg
            20                  25                  30
Phe Tyr Gly Lys Asn Ser Ser Tyr Val His Gly Gly Leu Asp Ser Asn
        35                  40                  45
Gly Lys Pro Ala Asp Ala Val Tyr Gly Gln Lys Glu Ile His Arg Lys
    50                  55                  60
Val Met Ser Gln Asn Phe Thr Asn Cys His Thr Lys Ile Arg His Val
65                  70                  75                  80
Asp Ala His Ala Thr Leu Asn Asp Gly Val Val Val Gln Val Met Gly
                85                  90                  95
Leu Leu Ser Asn Asn Asn Gln Ala Leu Arg Arg Phe Met Gln Thr Phe
            100                 105                 110
Val Leu Ala Pro Glu Gly Ser Val Ala Asn Lys Phe Tyr Val His Asn
        115                 120                 125
Asp Ile Arg Tyr Gln Asp Glu Val Phe Gly Gly Phe Val Thr Glu Pro
    130                 135                 140
```

```
Gln  Glu  Glu  Ser  Glu  Glu  Val  Glu  Glu  Pro  Glu  Glu  Arg  Gln  Gln
145            150                      155                      160

Thr  Pro  Glu  Val  Val  Pro  Asp  Asp  Ser  Gly  Thr  Phe  Tyr  Asp  Gln  Ala
                    165                      170                 175

Val  Val  Ser  Asn  Asp  Met  Glu  Glu  His  Leu  Glu  Glu  Pro  Val  Ala  Glu
               180                      185                      190

Pro  Glu  Pro  Asp  Pro  Glu  Pro  Glu  Gln  Glu  Pro  Val  Ser  Glu
          195                      200                 205

Ile  Gln  Glu  Glu  Lys  Pro  Glu  Pro  Val  Leu  Glu  Thr  Ala  Pro  Glu
          210                 215                      220

Asp  Ala  Gln  Lys  Ser  Ser  Pro  Ala  Pro  Ala  Asp  Ile  Ala  Gln  Thr
225                 230                 235                           240

Val  Gln  Glu  Asp  Leu  Arg  Thr  Phe  Ser  Trp  Ala  Ser  Val  Thr  Ser  Lys
               245                      250                      255

Asn  Leu  Pro  Pro  Ser  Gly  Ala  Val  Pro  Val  Thr  Gly  Ile  Pro  His
               260                 265                      270

Val  Val  Lys  Val  Pro  Ala  Ser  Gln  Pro  Arg  Pro  Glu  Ser  Lys  Pro  Glu
          275                      280                 285

Ser  Gln  Ile  Pro  Pro  Gln  Arg  Pro  Gln  Arg  Asp  Gln  Arg  Val  Arg  Glu
     290                      295                 300

Gln  Arg  Ile  Asn  Ile  Pro  Pro  Gln  Arg  Gly  Pro  Arg  Pro  Ile  Arg  Glu
305                      310                 315                           320

Ala  Gly  Glu  Gln  Gly  Asp  Ile  Glu  Pro  Arg  Arg  Met  Val  Arg  His  Pro
               325                      330                      335

Asp  Ser  His  Gln  Leu  Phe  Ile  Gly  Asn  Leu  Pro  His  Glu  Val  Asp  Lys
               340                      345                      350

Ser  Glu  Leu  Lys  Asp  Phe  Phe  Gln  Ser  Tyr  Gly  Asn  Val  Val  Glu  Leu
          355                      360                      365

Arg  Ile  Asn  Ser  Gly  Gly  Lys  Leu  Pro  Asn  Phe  Gly  Phe  Val  Val  Phe
     370                      375                      380

Asp  Asp  Ser  Glu  Pro  Val  Gln  Lys  Val  Leu  Ser  Asn  Arg  Pro  Ile  Met
385                      390                      395                      400

Phe  Arg  Gly  Glu  Val  Arg  Leu  Asn  Val  Glu  Glu  Lys  Lys  Thr  Arg  Ala
               405                      410                      415

Ala  Arg  Glu  Gly  Asp  Arg  Arg  Asp  Asn  Arg  Leu  Arg  Gly  Pro  Gly  Gly
               420                 425                      430

Pro  Arg  Gly  Gly  Leu  Gly  Gly  Gly  Met  Arg  Gly  Pro  Pro  Arg  Gly  Gly
          435                      440                 445

Met  Val  Gln  Lys  Pro  Gly  Phe  Gly  Val  Gly  Arg  Gly  Leu  Ala  Pro  Arg
     450                      455                 460

Gln  Glx
465
```

( 2 ) INFORMATION FOR SEQ ID NO:10:

( i ) SEQUENCE CHARACTERISTICS:
        ( A ) LENGTH: 2129 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2129

( x i ) SEQUENCE DESCRIPTION: SEQ ID NO:10:

| | | | | | |
|---|---|---|---|---|---|
| GCTTGCCTGT | CAGGTCGACT | CTAGAGCCCG | GGTACCGAGC | TCGAATTCGG | CGGGGTTTGT | 60
| ACTATCCTCG | GTGCTGTGGT | GCAGAGCTAG | TTCCTCTCCA | GCTCAGCCGC | GTAGGTTTGG | 120
| ACATATTTAC | TCTTTTCCCC | CCAGGTTGAA | TTGACCAAAG | CAATGGTGAT | GGAGAAGCCT | 180
| AGTCCCCTGC | TGGTCGGGCG | GGAATTTGTG | AGACAGTATT | ACACACTGCT | GAACCAGGCC | 240
| CCAGACATGC | TGCATAGATT | TTATGGAAAG | AACTCTTCTT | ATGTCCATGG | GGGATTGGAT | 300
| TCAAATGGAA | AGCCAGCAGA | TGCAGTCTAC | GGACAGAAAG | AAATCCACAG | GAAAGTGATG | 360
| TCACAAAACT | TCACCAACTG | CCACACCAAG | ATTCGCCATG | TTGATGCTCA | TGCCACGCTA | 420
| AATGATGGTG | TGGTAGTCCA | GGTGATGGGG | CTTCTCTCTA | ACAACAACCA | GGCTTTGAGG | 480
| AGATTCATGC | AAACGTTTGT | CCTTGCTCCT | GAGGGGTCTG | TTGCAAATAA | ATTCTATGTT | 540
| CACAATGATA | TCTTCAGATA | CCAAGATGAG | GTCTTTGGTG | GGTTTGTCAC | TGAGCCTCAG | 600
| GAGGAGTCTG | AAGAAGAAGT | AGAGGAACCT | GAAGAAAGCA | GCAAACACCT | GAGGTGGTAC | 660
| CTGATGATTC | TGGAACTTTC | TATGATCAGG | CAGTTGTCAG | TAATGACATG | GAAGAACATT | 720
| TAGAGGAGCC | TGTTGCTGAA | CCAGAGCCTG | ATCCTGAACC | AGAACCAGAA | CAAGAACCTG | 780
| TATCTGAAAT | CCAAGAGGAA | AAGCCTGAGC | CAGTATTAGA | AGAAACTGCC | CCTGAGGATG | 840
| CTCAGAAGAG | TTCTTCTCCA | GCACCTGCAG | ACATAGCTCA | GACAGTACAG | GAAGACTTGA | 900
| GGACATTTTC | TTGGGCATCT | GTGACCAGTA | AGAATCTTCC | ACCCAGTGGA | GCTGTTCCAG | 960
| TTACTGGGAT | ACCACCTCAT | GTTGTTAAAG | TACCAGCTTC | ACAGCCCGT | CCAGAGTCTA | 1020
| AGCCTGAATC | TCAGATTCCA | CCACAAAGAC | CTCAGCGGGA | TCAAAGAGTG | CGAGAACAAC | 1080
| GAATAAATAT | TCCTCCCCAA | AGGGGACCCA | GACCAATCCG | TGAGGCTGGT | GAGCAAGGTG | 1140
| ACATTGAACC | CCGAAGAATG | GTGAGACACC | CTGACAGTCA | CCAACTCTTC | ATTGGCAACC | 1200
| TGCCTCATGA | AGTGGACAAA | TCAGAGCTTA | AGATTTCTT | TCAAAGTTAT | GGAAACGTGG | 1260
| TGGAGTTGCG | CATTAACAGT | GGTGGGAAAT | TACCCAATTT | TGGTTTTGTT | GTGTTTGATG | 1320
| ATTCTGAGCC | TGTTCAGAAA | GTCCTTAGCA | ACAGGCCCAT | CATGTTCAGA | GGTGAGGTCC | 1380
| GTCTGAATGT | CGAAGAGAAG | AAGACTCGAG | CTGCCAGGGA | AGGCGACCGA | CGAGATAATC | 1440
| GCCTTCGGGG | ACCTGGAGGC | CCTCGAGGTG | GGCTGGGTGG | TGGAATGAGA | GGCCCTCCCC | 1500
| GTGGAGGCAT | GGTGCAGAAA | CCAGGATTTG | GAGTGGGAAG | GGGGCTTGCG | CCACGGCAGT | 1560
| AATCTTCATG | GATCTTCATG | CAGCCATACA | AACCCTGGTT | CCAACAGAAT | GGTGAATTTT | 1620
| CGACAGCCTT | TGGTATCTTG | GAGTATGACC | CCAGTCTGTT | ATAAACTGCT | TAAGTTTGTA | 1680
| TAATTTTACT | TTTTTTGTGT | GTTAATGGTG | TGTGCTCCCT | CTCCCTCTCT | TCCCTTTCCT | 1740
| GACCTTTAGT | CTTTCACTTC | CAATTTTGTG | GAATGATATT | TTAGGAATAA | CGGACTTTTA | 1800
| CCCGAATTCG | TAATCATGGT | CATAGCTGTT | TCCGTGTGAA | ATTGTTATCC | GCTCACAATT | 1860
| CCACACAACA | TACGAGCCGG | AAGCATAAAG | TGTAAAGCCT | GGGGTGCCTA | ATGAGTGAGC | 1920
| TAACTCACAT | TAATTGCGTT | GCGCTCACTG | CCCGCTTTCC | AGTCGGGAAA | CCTGTCGTGC | 1980
| CAGCGCATTA | ATGAATCGGC | CAACGCGCGG | GGAGAGGCGG | TTTGCGTATT | GGGCGCCAGG | 2040
| GTGGTTTTCT | TTTCACCAGT | GAGACGGGCA | ACAGCTGATT | GCCCTTCACC | GCTGGCCCTG | 2100
| AGAGAGTTGC | AGCAAGCGGT | CCACGCTGG | | | | 2129

PEPTIDES CAPABLE OF BINDING TO THE GAP PROTEIN SH3 DOMAIN, NUCLEOTIDE SEQUENCES CODING THEREFOR, AND PREPARATION AND USE THEREOF

The present invention relates to novel peptide and nucleotide sequences and to their pharmaceutical use. More particularly, the invention relates to peptides which are able to bind to the SH3 domain of the GAP protein.

The products of the Ras genes, generally designated p21 proteins, play a key role in the control of cell division in all the eucaryotic organisms which have been investigated. Certain specific modifications of these proteins cause them to lose their normal control and lead them to become oncogenic. Thus, a large number of human tumours are associated with the presence of modified Ras genes. In the same way, overexpression of these p21 proteins can lead to deregulation of cell proliferation. Taken overall, the p21 proteins are implicated in 30% of human cancers.

An understanding of the precise role of these p21 proteins therefore constitutes one of the main objectives of research in the sphere of oncology.

The model which is currently available for explaining the function of the p21 proteins rests on analogies which they share with the G transduction proteins. In cells, there is an equilibrium between the active p21 proteins, which are bound to GTP, and the inactive forms, which have bound GDP. In a quiescent cell, where the p21 proteins are not required, most of these proteins are in the GDP form. When the cell is stimulated, the nucleotide exchange factor, GEF, becomes more active and promotes removal of the GDP and its replacement by GTP. The protein then adopts an active conformation which enables it to recognize and stimulate its effector, the GAP protein, "GTPase-activating protein", which is in all probability associated with other proteins. The p21-GTP-GAP complex probably interacts, in turn, with one or more other proteins, thereby resulting in transmission of the signal which leads to a biological response by the cell. The association of p21-GTP with GAP simultaneously triggers hydrolysis of the GTP and return of the p21 to its inactive form.

In the case of the oncogenic p21 proteins, the mutation which they carry prevents return to the inactive state. In this latter case, the equilibrium is displaced towards the active form of p21.

This complex equilibrium between the active and inactive forms of p21 is controlled at one and the same time by factors which are inherent to the biochemical properties of the p21 proteins (relative affinity for GDP and GTP, rate of nucleotide exchange, etc.) and external factors which modulate their activity, such as, in particular, the GAP protein.

The GAP protein is a cytosolic protein which is present in all eucaryotic organisms and which possesses, therefore, the property of strongly accelerating hydrolysis of the GTP which is bound to the normal p21 protein (Trahey and McCormick 1987). It possesses two domains which are responsible for separate functions. Its carboxyterminal end carries the catalytic activity which binds the p21 proteins and increases their GTPase activity. At its other end, downstream of the amino terminal part, there is a juxtaposition of domains SH2 and SH3, which are able to participate in interactions with other proteins.

Currently, two proteins are known which interact with the GAP protein. These proteins are designated p62 and p190, being respectively of 62 kDa and 190 kDa molecular weight. Since these two proteins are immunoprecipitated by antibodies directed against different epitopes of GAP, they evidently form a specific complex with GAP. It is known, in particular, that the p62 protein interacts with the GAP protein in the SH2 region.

As far as the SH3 domain is concerned, in particular, its presence in various proteins such as the Cγ phospholipases (PLC-γ), the p85 subunit of 3-phosphatidylinositol kinase and the grb-2 protein, all of which are implicated in transduction of the Ras p21 signal, suggests that this domain is of particular importance for directing protein/protein interactions and therefore essential to the function of the corresponding protein and/or its location in the cell. In the particular case of the GAP protein, this SH3 domain could, therefore, also participate in transduction of the Ras signal. It is obvious that an understanding of the precise role of this SH3 domain would be particularly valuable at the therapeutic level.

The object of the present invention is precisely that of contributing to elucidation of the contribution of the SH3 domain to transduction of the Ras signal.

Thus, the Applicant has demonstrated the existence of proteins which are able to attach to the GAP protein by binding directly to its SH3 domain.

More specifically, the present invention results from the identification, isolation and characterization of proteins which are able to interact with the SH3 domain of the GAP protein. It also results from the structural characterization of these proteins by identifying corresponding peptide sequences.

More especially, the polypeptide of the invention, which polypeptide is able to interact with the SH3 domain of the GAP protein, comprises all or part of a peptide sequence selected from among the sequences SEQ ID No. 1, SEQ ID No. 2, SEQ ID No. 3, SEQ ID No. 4, SEQ ID No. 5 and SEQ ID No. 9, or of a derivative of these sequences.

Within the meaning of the present invention, the term derivative denotes any molecule which is obtained by genetic and/or chemical modification of the polypeptide according to the invention and which retains the sought-after activity. Genetic and/or chemical modification is understood to mean any mutation, substitution, deletion, addition and/or modification of one or more residues. Such derivatives can be generated for different purposes such as, in particular, that of increasing the affinity of the peptide for its site of interaction, that of improving the levels at which it is produced, that of increasing its resistance to proteases, that of increasing its therapeutic efficacy or of reducing its side-effects, or that of conferring on it novel pharmacokinetic and/or biological properties.

It can also denote fragments of the abovementioned sequences of derivatives of these fragments. Such fragments can be generated in different ways. In particular, they can be synthesized chemically, based on the sequence given in FIG. 1, using the peptide synthesizers known to the person skilled in the art. They can also be synthesized genetically by expressing a nucleotide sequence encoding the sought-after peptide in a cell host. In this case, the nucleotide sequence can be prepared chemically using an oligonucleotide synthesizer, based on the peptide sequence given in the present application and on the genetic code. The nucleotide sequence can also be prepared, using the sequence given in the present application, by enzymic restriction, ligation, cloning etc., in accordance with the techniques known to the person skilled in the art, or by screening DNA libraries with probes developed on the basis of SEQ ID No. 1.

According to one embodiment of the invention, the claimed peptide comprises SEQ ID No. 1, SEQ ID No. 2, SEQ ID No. 3 and/or SEQ ID No. 4.

Preferably, the polypeptide according to the invention has a molecular weight of the order of 68 kDa.

According to one embodiment of the invention, the polypeptide is a polypeptide of human origin comprising all or part of SEQ ID No. 5 or SEQ ID No. 9 or of one of their derivatives such as previously defined.

The polypeptide is, more especially, a polypeptide comprising SEQ ID No. 5.

More preferably, the polypeptide is a polypeptide represented by SEQ ID No. 9 or one of its derivatives.

Unexpectedly, this protein does not possess homology with another p68 protein which has already been identified as binding to the SH3 domain of Src. Its tyrosine motifs are not phosphorylated in growing cells or in cells which are in a state of mitosis.

Analysis of the protein SEQ. ID No. 9 reveals that the protein which is attached to the SR+H3 domain of the GAP protein, and which is designated G3BP, belongs to the hnRNP (heterologous nuclear ribonucleoproteins) family. More specifically, G3BP is a protein of 466 amino acids, which has an apparent molecular weight of 68 kDa and which contains several domains which are characteristic for proteins which bind to RNA:

RNP2 and RNP1 domains (amino acids 342 to 347)

4 RGG box (amino acids 435 to 449)

an acidic auxiliary domain (amino acids 144 to 221).

The invention also extends to peptides which are able to antagonize the interaction between G3BP and the SH3 domain of GAP. The activity of these peptides can be demonstrated in competition tests (cf. Example 2–3) or in tests involving interference with signals transduced by the Ras proteins.

The invention also relates to polyclonal or monoclonal antibodies or antibody fragments which are directed against a polypeptide as defined above. Such antibodies can be generated by methods known to the person skilled in the art. In particular, these antibodies can be prepared by immunizing an animal against a polypeptide whose sequence is selected from among SEQ ID No. 1, SEQ ID No. 2, SEQ ID NO. 3, SEQ ID NO. 4, SEQ ID No. 5 and SEQ ID No. 9 or any fragment or derivative of these sequences, removing blood and isolating the antibodies. These antibodies can also be generated by preparing hybridomas in accordance with the techniques known to the person skilled in the art.

The antibodies or antibody fragments of the invention can then be employed to regulate the activation state of the product of the Ras genes.

Moreover, these antibodies can also be employed to detect and/or assay a peptide according to the invention in biological samples and, therefore, to provide information on the activation state of the product of the Ras genes.

The invention also extends to antagonists, namely any peptide which is able to block the interaction of a polypeptide according to the invention with the SH3 domain of the GAP protein. Such peptides can be demonstrated in competition tests (cf. Example 2–3) or tests in which Ras activity is inhibited.

The present invention therefore renders it possible to generate polypeptides which are derived from the sequences identified above and also antibodies which are directed against these polypeptides or corresponding proteins which exhibit biological properties which are of interest with a view to pharmaceutical utilization.

The invention also provides non-peptide compounds, or compounds which are not exclusively peptide in nature, which can be used pharmaceutically. Thus, it is possible, on the basis of the active protein motifs described in the present application, to construct molecules which inhibit the p21 protein-dependent signal pathway and which are not exclusively peptide in nature and are compatible with pharmaceutical utilization. In this respect, the invention relates to the use of a polypeptide of the invention, such as described above, for preparing pharmacologically active non-peptide molecules, or pharmacologically active molecules which are not exclusively peptide in nature, by determining the structural elements of this polypeptide which are important for its activity and reproducing these elements by means of non-peptide structures or of structures which are not exclusively peptide in nature. The invention also relates to pharmaceutical compositions which comprise one or more molecules which have been prepared in this way.

The present invention also relates to any nucleic acid sequence encoding a polypeptide which is able to bind to the SH3 domain of the GAP protein. More preferably, it relates to a sequence comprising:

(a) all or part of SEQ ID No. 6, or SEQ ID No. 10 or one of their complementary strands, (b) any sequence which hybridizes with sequence (a) and encodes a polypeptide according to the invention, and (c) the sequences which are derived from sequences (a) and (b) on account of the degeneracy of the genetic code.

Preferably, it comprises sequence SEQ ID No. 6 and, more preferably, is represented by SEQ ID No. 10.

The different nucleotide sequences of the invention may or may not be of artificial origin. They can be genomic, cDNA or RNA sequences, hybrid sequences or synthetic or semi-synthetic sequences. These sequences can be obtained, for example, by screening DNA libraries (cDNA library or genomic DNA library) using probes which are designed on the basis of sequences presented above. Such libraries can be prepared from cells of different origins using conventional molecular biological techniques known to the person skilled in the art. The nucleotide sequences of the invention can also be prepared by chemical synthesis, in particular in accordance with the phosphoramidite method, or else by mixed methods including chemical or enzymic modification of sequences obtained by screening libraries.

These nucleotide sequences according to the invention may be used in the pharmaceutical domain, either for producing the polypeptides of the invention, or for constructing antisense sequences which can be used in gene therapy, or else for detecting and diagnosing, by means of hybridization experiments, the activity of the GAP protein in biological samples, or for isolating homologous sequences from other cell sources.

In order to produce the polypeptides of the invention, the above-defined nucleic acid sequences are generally placed under the control of signals which enable them to be expressed in a host cell. The choice of these signals (promoters, terminators, secretory leader sequence, etc.) may vary depending on the host cell employed. Preferably, these nucleotide sequences of the invention form part of a vector which can be autonomously replicating or one which integrates. More especially, autonomously replicating vectors can be prepared using sequences which replicate autonomously in the chosen host. Integrating vectors can be prepared, for example, using sequences which are homologous to certain regions of the host genome and which enable the vector to integrate by means of homologous recombination.

The host cells which can be used for producing the polypeptides of the invention can be either eucaryotic or procaryotic hosts. Suitable eucaryotic hosts which may be mentioned are animal cells, yeasts or fungi. In particular, yeasts which may be cited are the yeasts of the genera Saccharomyces, Kluyveromyces, Pichia, Schwanniomyces or Hansenula. Animal cells which may be cited are COS, CHO, C127, etc. cells. Fungi which may more particularly be cited are *Aspergillus spp.* or *Trichoderma spp.* The following bacteria are preferably used as procaryotic hosts: *E. coli*, Bacillus or Streptomyces.

The nucleic acid sequences according to the invention can also be employed to construct antisense nucleic acids which can be used as pharmaceutical agents. Inhibition of the expression of certain oncogenes by antisense nucleic acids has proved to be a useful strategy in understanding the role of these oncogenes and a particularly promising approach to achieving an anti-cancer treatment. Antisense oligonucleotides are small oligonucleotides which are complementary to the coding strand of a given gene and, for this reason, are able to hybridize specifically with the transcribed mRNA, inhibiting its translation into protein. Such oligonucleotides can be constituted by all or part of the nucleic acid sequences defined above. In general, they are sequences or fragments of sequences which are complementary to sequences encoding the peptides according to the invention. Such oligonucleotides can be obtained from the abovementioned sequences, by fragmentation, etc., or by chemical synthesis.

The invention also relates to the nucleotide probes, as nucleotide sequences, whether or not they are synthetic, which are able to hybridize with the nucleotide sequences defined above which encode a polypeptide of the invention, or with the corresponding mRNA. Such probes can be used in vitro as a diagnostic tool. Such probes have to be labelled in advance, and different techniques for doing this are known to the person skilled in the art. The hybridization conditions under which these probes can be used are the normal stringency conditions. These probes can also be used to detect and isolate homologous nucleic acid sequences which encode a polypeptide of the invention, using other cellular sources. As an illustration of these probes, mention may be made, more particularly, of the probes represented by SEQ ID No. 7 and SEQ ID No. 8, which are used in Example 3 below.

The invention furthermore relates to any pharmaceutical composition which comprises, as its active principle, at least one polypeptide as defined above.

The invention also relates to any pharmaceutical composition which comprises, as its active principle, at least one antibody and/or antibody fragment as defined above, as well as to any pharmaceutical composition which comprises, as its active principle, at least one antisense oligonucleotide as defined above.

Furthermore, it also relates to the pharmaceutical compositions in which the above-defined polypeptides, antibodies and oligonucleotides are attached to each other or to other active principles.

The pharmaceutical compositions according to the invention can be used to modulate activation of the p21 proteins and, as a result, to modulate proliferation of certain cell types. More especially, these pharmaceutical compositions are intended for treating cancers. Thus, numerous cancers have been associated with the presence of oncogenic Ras proteins. Of those cancers which most frequently contain mutated Ras genes, mention may be made, in particular, of adenocarcinomas of the pancreas, 90% of which contain a Ki-Ras oncogene whose twelfth codon is mutated (Almoguera et al., Cell 53 (1988) 549), adenocarcinomas of the colon and cancers of the thyroid (50%), or carcinomas of the lung and myeloid leukaemias (30%, Bos, J. L. Cancer Res. 49 (1989) 4682).

The invention also relates to the use of the above-described molecules for modulating, that is inhibiting, the activity of the p21 proteins. In particular, the invention relates to the use of all, or a fragment, of G3BP for interfering with the signals which are transduced by the products of the Ras genes. The protein fragments which are homologous with the hnRNPs are advantageously used to inhibit the binding of G3BP to its target RNAs. Sequences which are identical, or complementary, to these target RNAs can also be used for interfering with the signals which are transduced by the G3BP protein.

The invention also provides a process for detecting expression and/or overexpression of the G3BP protein in a biological sample. Such a process comprises, for example, bringing such a sample into contact with an antibody or antibody fragment according to the invention, detecting the antigen/antibody complexes, and comparing the results which are obtained with a standard sample. In such a process, the antibody can be in suspension or immobilized in advance on a support. This process can also comprise bringing the sample into contact with a nucleotide probe according to the invention, detecting the hybrids which are obtained, and comparing with those obtained in the case of a standard sample.

The present invention can be used in many ways in the therapeutic sphere: since the polypeptides, antibodies and nucleotide sequences of the invention are able to modulate the activity of the Ras genes, they thereby make it possible to intervene in the process of cancer development. Due to the fact that they are strongly expressed in striated skeletal muscle cells, these peptides probably also intervene in pathologies which are linked to a signalling defect such as diabetes, for example. Another aspect of the invention consists in using DNA or RNA nucleotide sequences which are able to interact with the claimed polypeptides. These sequences can be prepared using the method described in International Application WO 91/19813.

The invention can also be used in connection with the diagnosis and typing of cancers.

Other advantages of the present invention will be apparent from reading the following examples and figures, which are to be considered as being by way of illustration and not limiting.

FIGURES

FIG. 1: Effect of G3BP overexpression in NIH 3T3 fibroblasts on CAT activity.

Figure 2:
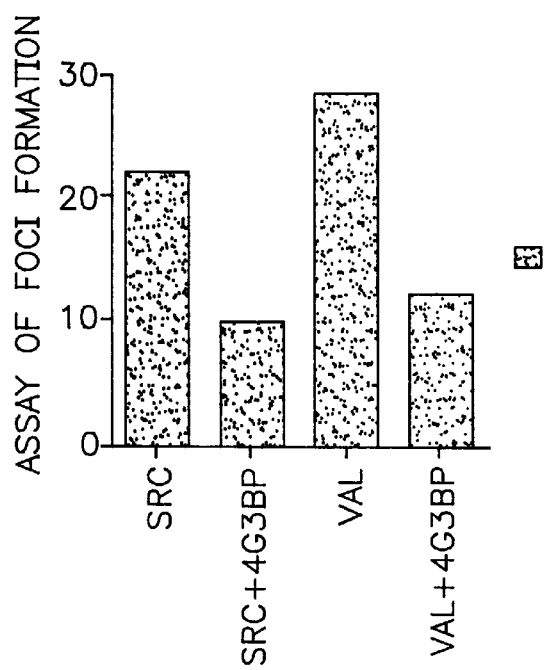

FIG. 2: Effect of G3BP overexpression in NIH 3T3 fibroblasts on the formation of foci which is induced by the Src and Ras oncogenes.

MATERIAL AND METHODS

General Cloning Techniques

The conventional methods which are used in molecular biology, such as preparative extractions of plasmid DNA, centrifugation of plasmid DNA in a caesium chloride gradient, electrophoresis on agarose or acrylamide gels, purification of DNA fragments by electroelution, extraction of proteins with phenol or phenol/chloroform, precipitation of DNA in a saline medium with ethanol or isopropanol, transformation into *Escherichia coli*, etc., are well known to the person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al., (eds), "Current Protocols in Molecular Biology", John Wiley & Sons, New York, 1987].

The restriction enzymes were supplied by New England Biolabs (Biolabs), Bethesda Research Laboratories (BRL) or Amersham and are used in accordance with the suppliers' recommendations.

Plasmid pGEX 2T is obtained commercially.

Enzymic amplification of DNA fragments by the technique termed PCR [polymerase-catalysed chain reaction, Saiki R. K. et al., Science 230 (1985) 1350–1354; Mullis K. B. et Faloona F. A., Meth. Enzym. 155 (1987) 335–350] is performed using a DNA thermal cycler (Perkin Elmer Cetus) in accordance with the manufacturer's specifications.

The nucleotide sequences are verified by the method developed by Sanger et al. [Proc. Natl. Acad. Sci. USA, 74 (1977) 5463–5467] using the kit distributed by Amersham.

In general, the normal stringency conditions for the hybridization experiments are the following: hybridization: 3×SCC in the presence of 5×Denhart's at 65° C.; washing: 0.5×SSC at 65° C.

EXAMPLE 1

Preparation of glutathione-S-transferase SH3 Fusion Proteins

The DNA sequences encoding the SH3 domains of the GAP (residues 275 to 350) and c-Src (residues 84 to 148) proteins are amplified by the P.C.R. technique and cloned into an expression vector, pGEX2T, between the BamHI and EcoRI restriction sites. The bacteria which have thus been transformed are cultured, induced with IPTG (1-thio-β-D-galactopyranoside) and lysed by sonication. The GST SH3 fusion proteins are purified by affinity chromatography on glutathione agarose beads (Pharmacia LKB biotech) and then eluted with 10 mM reduced glutathione.

EXAMPLE 2

1) Preparation of the Cell Lysates

ER22 cells (hamster fibroblasts which overexpress human EGF receptor) or NIH 3T3 cells which express C-Src pp60 (F-527) are cultured on DMEM medium (Dubelcco's modified Eagle medium), which is enriched with 10% foetal calf serum containing the antibiotic G418 (200 µg/ml) and 2 mM/l glutamine (5GIBCO-BRL), at 370° C. under 5% $CO_2$.

In each assay, the ER22 cells are cultured in 100 mm dishes until they become confluent and are then incubated without serum for 18 hours. Sodium orthovanadate is added to a final concentration of 100 µM and the incubation is continued for 30 minutes. EGF is then added directly to the medium to give a final concentration of 80 nM over a period of 10 minutes and at 37° C.

For certain assays, the mitotic cells are recovered by treating with 0.4 µg of nocodazole (SIGMA) per ml for 18 hours. They are rapidly washed with a phosphate-based saline buffer, recooled in ice and then solubilized at 4° C. over a period of 30 minutes in 1 ml of lysis buffer, HNTG (50 mM Hepes, pH 7.5, 150 mM NaCl, 1% Triton×100, 10% glycerol, 1 mM $MgCl_2$, 1 mM EGTA, in the presence of phosphatase inhibitors (1 mM $Na_3VO_4$, 10 mM $Na_4P_2O_7$ and 10 mM NaF) and protease inhibitors (1 µg/ml leupeptin, 1 µg/ml trypsin inhibitor, 1 µg/ml pepstatin A, 2 µg/ml aprotinine, 10 µg/ml benzamidine, 1 mM phenylmethanesulfonyl fluoride, 1 µg/ml 1 µg/ml antipain and 1 µg/ml chymostatin).

The lysates are clarified by centrifuging at 15,000 rpm for 10 min. The protein concentration is then determined (Biorad microtest).

2) Test for Direct Bonds

The whole of the cell lysate (200 µg) and the immunoprecipitated proteins are separated on a 7.5% sodium dodecyl sulphate polyacrylamide gel (SDS-PAGE) and then transferred on to a polyvinylidene difluoride membrane (PVDF, Millipore Corp.). Non-specific binding to the filters is blocked, at room temperature for 2 hours, with 2% skimmed milk in PBS containing 0.05% Tween 20. The filters are incubated with GST protein and the GST-SH3 proteins in blocking buffer at 4° C. for 12 h. After having been washed with PBS-0.05% Tween 20, the bound proteins are detected by incubating successively with an anti-GST monoclonal antibody (0.25 µg/ml) (Hybridolab Pasteur Inst.), an anti-mouse antibody conjugated to alkaline phosphatase and 5-bromo-4-chloro-3-indolyl phosphate toluidinium nitroblue tetrazolium salt (PROMEGA).

3) Competition Test

Synthetic peptides which correspond to sequences (275–305), (299–326), (317–326) and (320–350) of GAP SH3 or to the putative sequence of dynamine (RRAPAVPPARPGS), which binds to the SH3 domaine, are synthesized on an Applied Biosystems 431 A apparatus using FMOC chemistry. The purified p68 protein is isolated by electrophoresis on a sodium dodecyl sulphate polyacrylamide gel and transferred by electrophoresis on to a PVDF membrane. The membranes are incubated with increasing quantities of peptides. The peptide poly-L-proline (SIGMA) is used at 500 µM in a control reaction. After incubating for 1 h, the protein GST-GAP-SH3 (2 µg/ml) is added to each reaction medium. The filtrates are probed with an anti-GST monoclonal antibody as previously described.

4) Immunoprecipitation and Immunotransfer

The soluble cell lysates (3 mg) are clarified with 50 µl of protein A Sepharose CL-4B (Pharmacia Biotech) at 4° C. for 2 h. The clarified cell lysates are incubated with anti-phosphotyrosine monoclonal antibody (monoclonal antibody 4G10—Upstate Biotechnology Incorporated) at 4° C. for 4 h. 50 µl of protein A Sepharose are then added to the complex and the incubation is continued at 4° C. overnight. The immunoprecipitate material is washed 3 times with an HNTG buffer and solubilized in a sample of SDS buffer (100 µl). The complexes are then separated by SDS-PAGE and transferred by electrophoresis to PVDF membranes.

The membranes are incubated with phosphotyrosine monoclonal antibody in TBS (10 mM Tris, pH 7.4, 150 nM NaCl, 3% bovine serum albumin) and also incubated with second antibodies which are conjugated to alkaline phosphatase. Substrates for the alkaline phosphatase are then added for appropriate colour development.

5) Purification and Analysis of the Sequence Approximately $5.10^9$ ER22 cells are lysed in 200 ml of HNTG buffer. The lysate is centrifuged at 15,000 g for 15 min and diluted 5 times in an HNG buffer (50 mM Hepes, pH 7.5, 150 mM NaCl, 10% glycerol, 1 mM EGTA, phosphatase inhibitors and protease inhibitors). The lysate is incubated overnight with 6 ml of Fast Flow S-Sepharose which is equilibrated in the same buffer. The complex is transferred to a column (IBF—2.5×1.3 cm). The column is washed with 10 times its volume of buffer and the bound proteins are then eluted, at an elution rate of 60 ml/h, with a linear gradient of 60 ml of from 0 to 1 M NaCl in the same buffer. The fractions possessing binding activity, as determined under the conditions of Example 2.2 (0.15–0.37 M NaCl), are collected, diluted 10 times in an HNG buffer and loaded on to Heparin-Sepharose Cl-6B (3 ml) (Pharmacia LKB), which is preequilibrated with the same buffer at an elution rate of 24 ml/h. After having been washed with the HNG buffer, the column is eluted with a 24 ml gradient of from 0 to 1 M NaCl. Active fractions from the S Fast Flow chromatography are collected, diluted 4 times in an MES buffer (100 mM MES, pH 6.8, 1 mM MgSO$_4$, 1 mM EGTA) and transferred to an agarose ATP column (3 ml) (Sigma No. A9264) which has been preequilibrated with the MES buffer containing 50 mM NaCl at an elution rate of 6 ml/h. The column is then washed with 20 ml of MES buffer containing 50 mM NaCl and eluted at 30 ml/h with a linear gradient of from 50 mM to 2M NaCl in the MES buffer. The p68 protein elutes between 0.3M and 0.4M NaCl. The active fractions are collected, dialysed with 20 mM NH$_4$HCO$_3$, pH 8.3, and concentrated. After having been taken to dryness, the proteins are resuspended in an SDS buffer and separated by electrophoresis on a polyacrylamide gel. The gel is stained with Coomassie blue and the 68 kDA molecular weight band, corresponding to the SH$_3$ binding activity, is recovered. It is washed for 1 hour with the following solutions: water, water/methanol (90/10), water/CH$_3$CN (80/20) and water/CH$_3$CN (50/50).

The gel band, which contains the purified p68 protein, is then divided into small fragments and dried under a SPEED/VAC (SAVANT). 400 µl of a solution containing 25 mM Tris, pH 8.5, 1 mM EDTA, 0.05% SDS and 5 µg of Lys-c endoproteinase (Boehringer Mannheim) are added, and the whole is incubated overnight at 37° C. The hydrolysate is injected on to a reverse phase HPLC column (Vydac C18: 2.1×250 mm). The column is eluted in 150 minutes, at 0.2 ml/min, with a linear gradient of from 0 to 35% B (A:H$_{20}$+ 0.07% TFA, and B: CH$_3$CN+0.07% TFA) and the elution peaks observed at retention times of 113.7, 117.7 and 133.7 min are collected and sequenced directly using an Applied Biosystems 477A microsequencer. The corresponding peptide sequence obtained in this way is presented in SEQ ID No. 1, SEQ ID No. 2, SEQ ID No. 3 and SEQ ID No. 4. These sequences do not exhibit any homology with proteins referenced in the protein databases (PIR 33. Swiss-Prot 33 (intelligenetics)).

In order to determine whether the p68 protein is tyrosine-phosphorylated in the mitotic or non-synchronous cells, the proteins in the lysates derived from ER22 cells which are cultured in 10% foetal calf serum or from cells treated with nocodazole are immunoprecipitated with anti-phosphotyrosine antibodies, transferred to membranes and either immunodetected with anti-phosphotyrosine antibodies or incubated with either GST-GAP-SH3 or GST-Src-SH3 under the conditions described in Examples 2.2 and 2.4. As a control, the proteins of NIH 3T3 cells which have been transformed with an activated allele of c-Src (c-Src Y527F) are tested under the same conditions as those described for the ER22 proteins. The results which are obtained demonstrate that proteins are tyrosine-phosphorylated, more especially in the 60–70 kDa region. No binding to a phosphorylated p68 protein is detected in the ER22 cells using the GST-GAP-SH3 or GST-Src-SH3 probes. In the NIH3T3 cells (c-Src-Y527F), the GST-Src-SH3 probe binds to a tyrosine-phosphorylated protein of 68 kDa molecular weight whereas the GST-GAP-SH3 probe does not interact with any protein.

Competition experiments to confirm the functional involvement of this protein in the Ras signalling pathway were carried out under the conditions described in Example 2.3. The results which are obtained demonstrate that the peptides derived from GAP are able to block Ras-induced rupture of Xenopus egg germinal vesicles (GVBD); GAP SH3 peptides (299–326) and (317–326) are also able to block the interaction between the G3BP protein and GAP.

These results clearly confirm that the ability to block, or interfere with, the activity of the protein according to the invention constitutes a particularly promising, novel approach in the treatment of cancer.

EXAMPLE 3

Isolation of the Human SEQ ID No. 6 Sequence from a Human Placenta cDNA Library.

Sequences SEQ ID No. 7 and No. 8, which were based on peptide sequences SEQ ID No. 1 and SEQ ID No. 3, are used as probes. The DNA of the Clonetech HL1008B library was prepared and used in a PCR reaction. 30 amplification cycles were carried out under the following conditions: denaturation, 1 min at 94° C., annealing, 1 min between 35 and 40° C., and elongation, 1 min at 72° C. This reaction gives rise to a 1.3 kb DNA fragment one part of whose sequence is given by SEQ ID No. 6. A Northern Blot analysis demonstrates that the corresponding RNA (3.3 kb) is ubiquitous and is expressed very strongly in adult skeletal muscle.

EXAMPLE 4

Isolation of the SEQ. ID No. 10 Sequence, which Encodes Human p68, from a Human Placenta cDNA Library.

The two oligonucleotides (SEQ ID No. 7) and (SEQ ID No. 8) are used as primers for amplifying a cDNA in a human placenta library. The PCR was carried out using Perkin Elmer Amplitaq at an annealing temperature of 35° C. followed by a 1 min extension at 72° C. in the presence of 10% formamide. We amplified a cDNA fragment of 1164 bp. After cloning directly into a pMOSblue vector (Amersham), which contained forward and reverse –20 sequences, the fragment was sequenced using fluorescent probes. This PCR fragment was then employed as a probe for screening 10$^6$ phages from a human placenta λgt11 cDNA library (Clonetech). The probe was synthesized by the Amersham Rediprime system and the filters were incubated at 45° C. for 16 hours in hybridization buffer (6×SSC, 5×Denhardt's, 100 µg/ml salmon sperm, 0.25% SDS) containing the probe. The filters were then washed at room temperature for 1 hour and at hybridization temperature for 20 min in 2×SSC, 0.05% SDS. Eight positive clones were identified. Two of them were purified and their cDNA was digested with EcoRI in order to excise the inserts. They were subcloned into M13mpl8/EcoRI in order to be sequenced. The sequencing was carried out on fragments obtained by progressive deletion of the cDNA with exonuclease III (Nested Deletion Kit, Pharmacia Biotech). The size differences of the fragments were analysed by PCR amplification between the forward and reverse –20 primers of the M13 vector, and different size populations were selected for sequencing. By assembling the different sequences which were obtained, it was possible to reconstitute the entire open reading frame of p68.

EXAMPLE 5

Overexpression of G3BP in NIH 3T3 Fibroblasts

NIH 3T3 fibroblasts are transfected with a reporter gene, that of chloramphenicol acetyl transferase, which is placed under the control of Ras response elements which derive from the polyome virus enhancer. These elements are stimulated from 15 to 30 fold when the cells are transfected with an expression vector carrying the cDNA of the Src and Ras oncogenes. These stimulations are modified when the G3BP protein is expressed following cotransfection with an expression vector which contains a cDNA which corresponds to the open reading frame of the protein. The G3BP inhibits, in a dose-dependent manner, the CAT activity which is stimulated by Src and by the oncogenic form of Ras. This observation is presented in FIG. 1.

In the same way, expression of the G3BP protein opposes the formation of foci which is induced by the Src and Ras oncogenes. FIG. 2 gives an account of this observation.

These experiments clearly demonstrate the ability of G3BP to oppose the proliferative effects of the signals which are transduced by the normal or oncogenic Ras proteins.

We claim:

1. An isolated polypeptide which binds an SH3 domain of GAP protein, wherein the polypeptide comprises:
   a) a peptide sequence selected from among the sequences SEQ ID No. 2, SEQ ID No. 3, SEQ No. 4, SEQ ID No. 5 and SEQ ID No. 9, or
   b) SEQ ID No. 1.

2. The polypeptide according to claim 1 which comprises SEQ ID No. 1, SEQ ID No. 2, SEQ ID No. 3 or SEQ ID No. 4, or a combination thereof.

3. The polypeptide according to claim 1, characterized in that it has a molecular weight of the order of 68 kDa.

4. The polypeptide according to claim 1 of human origin.

5. The polypeptide according to claim 4 which comprises the sequence SEQ ID No. 5 or SEQ ID No. 9.

6. The polypeptide according to claim 1 having a sequence of SEQ. ID No. 9.

7. The polypeptide according to claim 1 having one or more tyrosine motifs, which are not phosphorylated in mitotic or growing cells.

* * * * *